United States Patent
Kouno et al.

(10) Patent No.: US 6,512,142 B1
(45) Date of Patent: Jan. 28, 2003

(54) POTASSIUM SORBATE GRANULATE AND PRODUCTION PROCESSES THEREOF

(75) Inventors: Mitsuhiro Kouno, Arai (JP); Masayuki Okada, Arai (JP); Kazuyuki Matsuoka, Nara (JP); Noboru Kamei, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/572,499

(22) Filed: May 18, 2000

(30) Foreign Application Priority Data

May 18, 1999 (JP) ............................ 11-137749

(51) Int. Cl.$^7$ ............................................. C07C 57/10
(52) U.S. Cl. ..................................................... 562/601
(58) Field of Search ......................................... 562/601

(56) References Cited

U.S. PATENT DOCUMENTS

| 3,758,563 A | | 9/1973 | Uematsu et al. |
| 4,133,857 A | * | 1/1979 | Takano et al. |
| 4,244,776 A | | 1/1981 | Noltner et al. |

FOREIGN PATENT DOCUMENTS

| DE | 2450184 A | | 4/1976 |
| GB | 1482477 | * | 8/1977 |
| JP | 49125316 | | 11/1974 |
| JP | 51127020 | | 11/1976 |
| JP | 52039619 | | 3/1977 |
| JP | 52048619 | | 4/1977 |
| JP | 52065215 | | 5/1977 |
| JP | 52125118 | | 10/1977 |
| JP | 10029960 | | 2/1998 |

OTHER PUBLICATIONS

Aldrich Handbook of Fine Chemicals, 1998–1999, p 1416.*
Derwent Abstract (Acc. No. 1987–097739) of JP 6204551A.
Kamei et al. (1987). Alkali sorbate preparation—by wet grinding sorbic acid with alkali in aqueous media.*

* cited by examiner

Primary Examiner—Ralph Gitomer
(74) Attorney, Agent, or Firm—Birch, Stewart, Kolasch & Birch, LLP

(57) ABSTRACT

A granulated product of potassium sorbate (i) has an overall pore volume of 0.3 ml/g or less, (ii) has an Na content of 450 ppm or less, or (iii) has an overall pore volume of 0.4 ml/g or less, or a granule hardness of 15% or less, and an Na content of 1000 ppm or less. The granulated product is obtained, for example, (i) by granulating a potassium sorbate aqueous solution through fluidized bed granulation drying, (ii) by neutralizing sorbic acid with a potassium sorbate having a molar ratio of Na to K (Na/K) of 0.0024 or less to yield potassium sorbate, and granulating the potassium sorbate, or (iii) by neutralizing sorbic acid with a potassium sorbate having a molar ratio of Na to K (Na/K) of 0.006 or less to yield potassium sorbate, and moisture-conditioning 100 parts by weight of the potassium sorbate with 1 to 8.5 parts by weight of water and 1 to 8 parts by weight of a water-soluble organic solvent and subjecting the resulting mixture to extrusion granulation. The granulated product of potassium sorbate has a highly stable hue over time.

7 Claims, No Drawings

POTASSIUM SORBATE GRANULATE AND PRODUCTION PROCESSES THEREOF

BACKGROUND OF THE INVENTION

1. Field of the Invention

This invention relates to a granulated product of potassium sorbate, to a process for producing the granulated product, and to a process for producing potassium sorbate. Such potassium sorbate is useful as, for example, a food additive.

2. Description of the Related Art

Sorbic acid and its salts have antiseptic and antimicrobial activities and are substantially nontoxic to the human body in normal concentrations in use. These compounds are therefore useful as food additives. In a variety of known processes for producing sorbic acid, a commercially important pathway is a process of polymerizing crotonaldehyde and ketene to form an intermediate polyester, and decomposing the polyester to yield sorbic acid. The thus-prepared sorbic acid contains various colored substances and other impurities, and is generally subjected to a treatment with activated carbon, distillation, recrystallization or another purification operation, and the purified sorbic acid is neutralized with potassium hydroxide to yield potassium sorbate. The prepared potassium sorbate is usually supplied as a granule obtained through a granulation operation.

Potassium sorbate generally shows a denser coloring, a stronger odor and a deteriorated quality with the passage of time from preparation. As possible solutions to the quality deterioration problem, different measures have been proposed. Such measures include a production technique of removing colored substances in the manufacture to improve the hue of the product immediately after the manufacture and a storage technique of sealing the product with an inert gas or of packing the product with a water-impermeable packaging after the manufacture.

However, these techniques do not always have commercially satisfactory effects and costs.

SUMMARY OF THE INVENTION

Accordingly, an object of the invention is to provide a granulated product of potassium sorbate having a satisfactory stability of hue over time, and to provide a production process of the granulated product.

Another object of the invention is to provide a process for producing potassium sorbate which is useful in the production of a granulated product of potassium sorbate having a satisfactory stability of hue over time.

The present inventors noted a synthesis operation of potassium sorbate in a series of production operations of potassium sorbate, and made intensive investigations on a relationship between deterioration of hue during a long-term storage of a granulated product of potassium sorbate and the amounts of impurities in the granulated product. They found a relation between an Na content of the granulated product and the degree of deterioration of hue. This lead the present inventors to a supposition that Na contaminating as an alkali into potassium sorbate is converted into a colored substance after a long-term storage. The inventors also made detailed consideration on a production process of potassium sorbate and found that the Na is predominantly derived from potassium hydroxide used as a material. Furthermore, the inventors determined an overall pore volume of a granulated potassium sorbate and made a detailed investigation on a relation between the overall pore volume and deterioration of hue after a long-time storage. As a result, they found a link between the overall pore volume and the degree of deterioration of hue. This finding indicates that the hygroscopicity of the granulated product is involved in the stability of hue. From these findings, it was speculated that Na-containing impurities in a granulated product of potassium sorbate absorb moisture to form colored substances. Likewise, the inventors found a link between the hardness and Na content of the granulated product and the stability of hue.

Based on the above finding, the present inventors further found that deterioration of hue in a granulated product of potassium sorbate can be prevented by specifying the overall pore volume and/or Na content of the granulated product within a specific range, or by specifying a granule hardness and the Na content of the granulated product within specific ranges. The present invention has been accomplished based on these findings.

Specifically, the present invention provides in an aspect a granulated product of potassium sorbate. The granulated product has (i) an overall pore volume of equal to or less than 0.3 ml/g, (ii) an Na content of equal to or less than 450 ppm, or (iii) an overall pore volume of equal to or less than 0.4 ml/g or a granule hardness of equal to or less than 15% and an Na content of equal to or less than 1000 ppm.

In another aspect, the invention provides a process for producing a granulated product of potassium sorbate. This process includes the step of subjecting an aqueous solution of potassium sorbate to fluidized bed granulation drying to yield the aforementioned granulated product of potassium sorbate.

In a further aspect, the invention provides a process for producing a granulated product of potassium sorbate. This process includes the steps of neutralizing sorbic acid with a potassium hydroxide having a molar ratio of Na to K (Na/K) of equal to or less than 0.0024 to yield potassium sorbate, and granulating the potassium sorbate.

The invention further provides, in yet another aspect, a process for producing a granulated product of potassium sorbate. The process includes the steps of neutralizing sorbic acid with a potassium hydroxide having a molar ratio of Na to K (Na/K) of equal to or less than 0.006 to yield potassium sorbate, moisture-conditioning 100 parts by weight of the potassium sorbate with 1 to 8.5 parts by weight of water and 1 to 8 parts by weight of a water-soluble organic solvent, and subjecting the moisture-conditioned potassium sorbate to extrusion granulation.

In addition and advantageously, the invention provides a process for producing potassium sorbate. The process includes the step of neutralizing sorbic acid with a potassium hydroxide having a molar ratio of Na to K (Na/K) of equal to or less than 0.006.

The term "ppm" as used herein means parts per million by weight.

Granular potassium sorbate (granulated product of potassium sorbate) is formed by adhesion of crystal masses with each other, and voids are formed between crystals in this process. The voids can be regarded as pores, and the diameters and volumes of the voids can be determined by a method for the determination of pore size for use in the evaluation of properties of catalysts. The term "pore(s)" as used herein also includes the voids.

The term "granule hardness" is defined in the following manner. A sample (a granule) is shifted through a standard sieve (Zenno; 500 μm) to yield a residue on sieve. About 100 g of the residue on sieve is weighed ($W_0$ g) and placed in a magnetic pot (100 mm in inner diameter, 100 mm in depth) of a variable horizontal roller ball mill with three pieces of a magnetic ball (30±2 mm in diameter, 35±3 g in weight). The sample is milled and pulverized by rotating the mill at a roller rotary rate of 75 rpm for 15 minutes. The pulverized sample is then shifted through the same sieve as above, and a powder passing the sieve is weighed (W g). The granule hardness is calculated according to the following equation:

Granule hardness (%)=$W/W_0 \times 100$

DESCRIPTION OF THE PREFERRED EMBODIMENT

The invented granulated product of potassium sorbate is distinguished by (i) having an overall pore volume of 0.3 ml/g or less (preferably 0.25 ml/g or less), (ii) having an Na content of 450 ppm or less (preferably 400 ppm or less), or (iii) having an overall pore volume of 0.4 ml/g or less (preferably 0.38 ml/g or less) or a granule hardness of 15% or less (preferably 12% or less), and an Na content of 1000 ppm or less (preferably 800 ppm or less). If the overall pore volume and Na content or granule hardness of the granulated product of potassium sorbate are out of the above-specified ranges, the granulated product is more markedly colored with time.

A granulated product having an overall pore volume of 0.3 ml/g or less is to have a highly stable hue over time even if the granulated product has a high Na content. A granulated product having an Na content of 450 ppm or less is to have a highly stable hue over time even if the granulated product has a large overall pore volume. This is probably because an Na impurity in the granulated product of potassium sorbate absorbs moisture to thereby form a colored substance. Specifically, a small overall pore volume can prevent the moisture absorption to thereby prevent the formation of colored substances, and a sufficiently minimized Na content yields a reduced amount of colored substances to thereby minimize the change of hue with time.

Even if (i) the granulated product has an overall pore volume of 0.3 ml/g or less, the Na content in the granulated product should be preferably minimized to, for example, 5000 ppm or less, preferably 2500 ppm or less, and more preferably 1500 ppm or less. Likewise, even if (ii) the granulated product has an Na content of 450 ppm or less, the overall pore volume of the granulated product should be preferably minimized to, for example, 2 ml/g or less, preferably 1 ml/g or less, and more preferably 0.5 ml/g or less.

The pore size distribution of the granulated product of potassium sorbate is not critical, but the total volume of pores having a pore size of 1 μm or less should preferably occupy 10% or more, and particularly preferably 40% or more of the overall pore volume.

The shape of the granulated product of potassium sorbate is not critical and is, for example, of spherical, elliptic spherical, massive, pellet, cylindrical, lenticular or indefinite shape.

The granulated product of potassium sorbate can be prepared by granulating a potassium sorbate aqueous solution or a powdered potassium sorbate. The potassium sorbate aqueous solution is obtained by reacting sorbic acid with potassium hydroxide in the presence of water, and the powdered potassium sorbate is obtained by concentrating and drying the potassium sorbate aqueous solution.

Sorbic acid for use in the invention is not critical and includes any sorbic acid obtained by a known or conventional technique. Such sorbic acid is generally prepared by a process comprising the steps of reacting crotonaldehyde with ketene in the presence of a catalyst (e.g., a fatty acid salt of zinc) to yield a polyester, and hydrolyzing the polyester with an acid or an alkali, or decomposing the polyester in a hot water. The above-prepared sorbic acid generally contains impurities and requires a purification operation for removing the impurities. If a tar content is removed by dissolving the sorbic acid in a sodium hydroxide aqueous solution in the purification operation, the Na content should be preferably removed and minimized in subsequent operations. For example, when the sorbic acid is dissolved in a sodium hydroxide aqueous solution to remove a tar content and the treated sorbic acid is acidified with hydrochloric acid to precipitate a free sorbic acid, the Na content as sodium chloride may contaminate the sorbic acid. In this case, the solubility of sorbic acid in water is about 0.3% by weight at around atmospheric temperatures, and the Na content can be removed at a low attrition rate by washing the sorbic acid with water.

A reaction (a neutralization reaction) of sorbic acid with potassium hydroxide is performed in the presence of water. For example, potassium sorbate can be obtained by mixing an aqueous slurry of sorbic acid with a potassium hydroxide aqueous solution. The reaction is performed, for example, at a temperature ranging from about 0° C. to 30° C. at pH of the reaction mixture in the reaction of about 8 to 13. The pH at the completion of the reaction should be preferably adjusted to about 11. The reaction can be conducted in any of a continuous system, a semi-batch system or a batch system.

The potassium sorbate or potassium sorbate aqueous solution can be granulated according to any known or conventional technique. Such granulation techniques include, but are not limited to, extrusion granulation (piston granulation), fluidized bed granulation drying, spray drying, tumbling granulation, oscillating granulation, and compression molding. The extrusion granulation technique comprises the steps of moisture-conditioning a powdered potassium sorbate with a moisture conditioner and extruding the moisture-conditioned potassium sorbate, and the fluidized bed granulation drying technique includes the steps of spraying an queues solution with hot air to form a fluidized bed and performing drying and granulation operations concurrently. Such moisture conditioners for use in the extrusion granulation include, for example, water; methanol, and other alcohols, and other water-soluble organic solvents; and mixtures of these solvents.

When granules are obtained by the extrusion granulation technique, the resulting potassium sorbate granules generally have an overall pore volume of 0.2 ml/g or more. The overall pore volume, pore size distribution and/or granule hardness can be finely adjusted by appropriately selecting the type and amount of the moisture conditioner used and an extruding pressure. The fluidized bed granulation drying technique can usually produce a granulated potassium sorbate having an overall pore volume of 0.3 ml/g or less. The drying (granulation) rate, the overall pore volume and pore size distribution of the granulated product can be adjusted by appropriately controlling the amount of sprayed potassium sorbate aqueous solution, and the temperature and volume of the hot air for drying.

The invented granulated product of potassium sorbate can be obtained according to the above process by, for example, appropriately selecting the Na content of a potassium hydroxide for use in the neutralization reaction and the granulation technique or granulation condition of potassium sorbate.

For example, the granulated product of potassium sorbate (i) having an overall pore volume of 0.3 ml/g or less can be prepared by subjecting a potassium sorbate aqueous solution to fluidized bed granulation drying operation. In the fluidized bed granulation drying, a hot air for drying is supplied at a flow rate of about 0.1 to 10 m/sec, and preferably about 0.5 to 5 m/sec at a temperature of about 100° C. to 160° C., and preferably about 105° C. to 140° C. The internal temperature of the fluidized bed is, for example, about 45° C. to 100° C. and preferably about 50° C. to 80° C.

The granulated product of potassium sorbate (ii) having an Na content of 450 ppm or less can be prepared by neutralizing sorbic acid with a potassium hydroxide having a molar ratio of Na to K (Na/K) of 0.0024 or less and preferably 0.0022 or less to yield potassium sorbate, and granulating the prepared potassium sorbate. In this case, the granulation technique is not critical, and any of above-mentioned techniques can be employed. The potassium hydroxide having a molar ratio of Na to K (Na/K) of 0.0024 or less can be selected from commercially available potassium hydroxide products. Such commercially available potassium hydroxide products are to have an Na content not exceeding 1% by weight according to Japanese Industrial Standards (JIS), and generally have an Na content of about 0.07 to 0.3% by weight.

The granulated product of potassium sorbate (iii) having an overall pore volume of 0.4 ml/g or less, or a granule hardness of 15% or less, and an Na content of 1000 ppm or less can be prepared, for example, in the following manner. Sorbic acid is neutralized with a potassium hydroxide having a molar ratio of Na to K (Na/K) of 0.006 or less and preferably 0.004 or less to yield potassium sorbate, and 100 parts by weight of the prepared potassium sorbate is subjected to moisture-conditioning with about 1 to 8.5 parts by weight, preferably about 1 to 8 parts by weight, and more preferably about 4 to 8 parts by weight of water, and about 1 to 8 parts by weight, preferably about 3 to 7 parts by weight of a water-soluble organic solvent such as methanol, and the treated potassium sorbate is then subjected to extrusion granulation.

The hardness of granules obtained by extrusion granulation partially depends on the properties of a powdered potassium sorbate before granulation. Specifically, a relatively fine powder will yield a hard granule, and a coarse powder will yield a fragile granule under the same moisture-conditioning condition. If granules are obtained from the same powder, the use of larger amounts of water will yield a hard granule after drying. However, an excessively large amount of water (e.g., water in a proportion of more than 8.5 parts by weight to 100 parts by weight of potassium sorbate) invites adhesion of granulated wet granules with each other to thereby deteriorate productivity. Hard granules can be also obtained by applying a high consolidation to a material powder during granulation operation. For example, such a hard granule can be obtained by reducing a diameter of mesh of molding screen. By appropriately selecting each of various procedure conditions in the extrusion granulation operation, a highly hard granule having a granule hardness of 15% or less can be prepared.

To produce granules having a highly stable hue over the long term, any of granulation techniques such as extrusion granulation can be employed when a potassium hydroxide having a low Na content is used. However, the fluidized bed granulation drying technique can be advantageously employed when a potassium hydroxide having a large Na content is used.

The invented potassium sorbate granules exhibit a markedly minimized coloring over long time after preparation and are suitable as food additives for long-term preservation. The prepared granulated products of potassium sorbate can be used as preservatives in foods such as fish paste products, butters, cheeses, bean pastes, and jams.

The invented granulated product of potassium sorbate has an overall pore volume and/or an Na content, or has a granule hardness and an Na content in specific ranges and exhibits a markedly minimized change of hue after long-term storage and has a highly stable hue over time. This is provably because the formation of colored substances induced by absorbed moisture and Na impurities is reduced.

The invented process for producing a granulated product of potassium sorbate can easily and efficiently produce a granulated product of potassium sorbate having a highly stable hue over time.

In addition, the invented process for producing potassium sorbate can produce a potassium sorbate product which is useful for the production of a granulated product of potassium sorbate having a highly stable hue over time.

The present invention will now be illustrated in further detail with reference to several inventive examples and comparative examples below, which are not intended limiting the scope of the invention. The granule hardness in the examples and comparative examples was determined by the following determination method.

Method of Granule Hardness Determination

Instrument: variable horizontal roller ball mill (100 mm in inner diameter and 100 mm in depth of a magnetic pot)

Condition: roller rotation rate: 75 rpm magnetic ball: three pieces, 30±2 mm in diameter, 35±3 g in weight Procedure:
(1) A sample (granule) was sifted through a predetermined standard sieve (Zenno: 500 Ξm)
(2) About 100 g ($W_0$ g) of the residue on sieve obtained in the above step (1) was placed in a magnetic pot with three pieces of the magnetic ball, and the residue was pulverized by rotating the pot for 15 minutes.
(3) The pulverized sample was taken out from the pot, and was shifted through the same sieve used in the step (1), and a powder passing the sieve was weighed (W g). The granule hardness was calculated according to the following equation:

Granule hardness (%)=$W/W_0 \times 100$

EXAMPLE 1

A purified sorbic acid was put into distilled water in a reactor and was stirred to yield a slurry. A 49% by weight potassium hydroxide aqueous solution was added dropwise to the slurry to neutralize the slurry. The sorbic acid and potassium hydroxide aqueous solution were intermittently fed to the reactor so as to maintain pH of the reaction mixture in a range from 8 to 13, and ultimately, 2.22 parts by weight of sorbic acid and 2.27 parts by weight of the potassium hydroxide aqueous solution to 1 part by weight of the distilled water initially added were reacted over 3 hours plus. The temperature of the reaction mixture during reaction was maintained at 25° C., and after the completion of reaction, pH of the reaction mixture was adjusted to 11 with a 10% by weight potassium hydroxide aqueous solution. The 49% by weight potassium hydroxide aqueous solution for use in the reaction had an Na content of 700 ppm and a molar ratio of Na to K (Na/K) of 0.0034.

The above-prepared potassium sorbate aqueous solution was dried to a moisture content of 0.1% by weight or less with a vacuum dryer (e.g., a double pipe dryer, a trough dryer) to yield a powdered potassium sorbate. The powder had an Na content of 550 ppm. A total of 100 parts by weight of the powdered potassium sorbate was subjected to moisture-conditioning with 7.0 parts by weight of water and 6.0 parts by weight of methanol, and the resulting mixture was granulated with a extrusion (piston) granulator.

The pore size distribution of the above-prepared granule was determined by the method of mercury penetration, and the granule was found to have an overall pore volume of 0.35 ml/g and a proportion of pores having a pore size of 1 $\mu$m or less of 50% relative to the overall pore volume. The granule had an Na content of 550 ppm and a moisture content of 0.05% by weight. In 8.6 ml of distilled water, 2 g of the granule was dissolved, and the light transmittance (color valency) of the resulting solution at a wavelength of 430 nm was determined with a spectrophotometer using distilled water as a reference. The solution was found to have a light transmittance at 430 nm of 96.0%.

The above-prepared granulated potassium sorbate was placed in a polyethylene bag, and the bag was sealed and was stored at room temperature of 20° C. for 2 years. After the storage, the granulated potassium sorbate was found to have a moisture content of 0.2% by weight and a light transmittance at 430 nm of 94.0%.

EXAMPLE 2

A potassium sorbate aqueous solution was prepared in the same manner as in Example 1, except that a 49% by weight aqueous solution of potassium hydroxide having an Na content of 1500 ppm and a molar ratio of Na to K (Na/K) of 0.0073 was used in the reaction.

The aqueous solution was dried and granulated with a fluidized bed granulation dryer at an initial hot air temperature of 120° C. blowing at a flow rate of 1 m/sec at an internal temperature of the fluidized bed of 65° C. to yield a granulated potassium sorbate. The granule had an overall pore volume of 0.21 ml/g and a proportion of pores having a pore size of 1 $\mu$m or less of 20% relative to the overall pore volume. The granule had an Na content of 1200 ppm and a moisture content of 0.05% by weight. A total of 2 g of the granule was dissolved in 8.6 ml of distilled water, and the light transmittance (color valency) of the resulting solution at a wavelength of 430 nm was determined with a spectrophotometer using distilled water as a reference. The solution was found to have a light transmittance at 430 nm of 96.2%.

The above-prepared granulated potassium sorbate was placed in a polyethylene bag, and the bag was sealed and was stored at room temperature of 20° C. for 2 years. After the storage, the granulated potassium sorbate was found to have a moisture content of 0.2% by weight and a light transmittance at 430 nm of 92.1%.

EXAMPLE 3

A granulated potassium sorbate was prepared in the same manner as in Example 1, except that a 49% by weight aqueous solution of potassium hydroxide having an Na content of 400 ppm and a molar ratio of Na to K (Na/K) of 0.0019 was used in the reaction.

The granule had an overall pore volume of 0.35 ml/g and a proportion of pores having a pore size of 1 $\mu$m or less of 50% relative to the overall pore volume. The granule had an Na content of 350 ppm and a moisture content of 0.05% by weight. A total of 2 g of the granule was dissolved in 8.6 ml of distilled water, and the light transmittance (color valency) of the resulting solution at a wavelength of 430 nm was determined with a spectrophotometer using distilled water as a reference. The solution was found to have a light transmittance at 430 nm of 96.2%.

The above-prepared granulated potassium sorbate was placed in a polyethylene bag, and the bag was sealed and was stored at room temperature of 20° C. for 2 years. After the storage, the granulated potassium sorbate was found to have a moisture content of 0.1% by weight and a light transmittance at 430 nm of 95.8%.

COMPARATIVE EXAMPLE 1

A granulated potassium sorbate was prepared in the same manner as in Example 1, except that a 49% by weight aqueous solution of potassium hydroxide having an Na content of 2000 ppm and a molar ratio of Na to K (Na/K) of 0.0097 was used in the reaction.

The granule had an overall pore volume of 0.35 ml/g and a proportion of pores having a pore size of 1 $\mu$m or less of 50% relative to the overall pore volume. The granule had an Na content of 1500 ppm and a moisture content of 0.05% by weight. A total of 2 g of the granule was dissolved in 8.6 ml of distilled water, and the light transmittance (color valency) of the resulting solution at a wavelength of 430 nm was determined with a spectrophotometer using distilled water as a reference. The solution was found to have a light transmittance at 430 nm of 96.1%.

The above-prepared granulated potassium sorbate was placed in a polyethylene bag, and the bag was sealed and was stored at room temperature of 20° C. for 2 years. After the storage, the granulated potassium sorbate was found to have a moisture content of 0.41% by weight and a light transmittance at 430 nm of 70.2%.

COMPARATIVE EXAMPLE 2

A granulated potassium sorbate was prepared in the same manner as in Example 1, except that 9.0 parts by weight of water and 9.0 parts by weight of methanol relative to 100 parts by weight of a powdered potassium sorbate were used for moisture-conditioning.

The granule had an overall pore volume of 0.42 ml/g and a proportion of pores having a pore size of 1 $\mu$m or less of 40% relative to the overall pore volume. The granule had an Na content of 550 ppm and a moisture content of 0.05% by weight. A total of 2 g of the granule was dissolved in 8.6 ml of distilled water, and the light transmittance (color valency) of the resulting solution at a wavelength of 430 nm was determined with a spectrophotometer using distilled water as a reference. The solution was found to have a light transmittance at 430 nm of 96.3%.

The above-prepared granulated potassium sorbate was placed in a polyethylene bag, and the bag was sealed and was stored at room temperature of 20° C. for 2 years. After the storage, the granulated potassium sorbate was found to have a moisture content of 0.6% by weight and a light transmittance at 430 nm of 72.4%.

COMPARATIVE EXAMPLE 3

A granulated potassium sorbate was prepared in the same manner as in Comparative Example 1, except that 9.0 parts by weight of water and 9.0 parts by weight of methanol relative to 100 parts by weight of a powdered potassium sorbate were used for moisture-conditioning.

The granule had an overall pore volume of 0.41 ml/g and a proportion of pores having a pore size of 1 $\mu$m or less of 40% relative to the overall pore volume. The granule had an Na content of 1500 ppm and a moisture content of 0.05% by weight. A total of 2 g of the granule was dissolved in 8.6 ml of distilled water, and the light transmittance (color valency) of the resulting solution at a wavelength of 430 nm was determined with a spectrophotometer using distilled water as a reference. The solution was found to have a light transmittance at 430 nm of 96.0%.

The above-prepared granulated potassium sorbate was placed in a polyethylene bag, and the bag was sealed and was stored at room temperature of 20° C. for 2 years. After the storage, the granulated potassium sorbate was found to have a moisture content of 0.9% by weight and a light transmittance at 430 nm of 56.6%.

EXAMPLE 4

A powdered potassium sorbate was prepared in the same manner as in Example 1. A total of 100 parts by weight of the powdered potassium sorbate was subjected to moisture-conditioning with 8.0 parts by weight of water and 5.0 parts by weight of methanol, and the resulting mixture was granulated with a extrusion granulator.

The granulated product had a hardness of 10.0%, an Na content of 550 ppm and a moisture content of 0.05% by weight. A total of 2 g of the granule was dissolved in 8.6 ml of distilled water, and the light transmittance (color valency) of the resulting solution at a wavelength of 430 nm was determined with a spectrophotometer using distilled water as a reference. The solution was found to have a light transmittance at 430 nm of 96.0%.

The above-prepared granulated potassium sorbate was placed in a polyethylene bag, and the bag was sealed and was stored at room temperature of 20° C. for 2 years. After the storage, the granulated potassium sorbate was found to have a moisture content of 0.2% by weight and a light transmittance at 430 nm of 94.5%.

COMPARATIVE EXAMPLE 4

A granulated potassium sorbate was prepared in the same manner as in Example 4, except that 3.0 parts by weight of water and 8.2 parts by weight of methanol relative to 100 parts by weight of a powdered potassium sorbate were used for moisture-conditioning.

The granulated product had a hardness of 20.0%, an Na content of 550 ppm and a moisture content of 0.05% by weight. A total of 2 g of the granule was dissolved in 8.6 ml of distilled water, and the light transmittance (color valency) of the resulting solution at a wavelength of 430 nm was determined with a spectrophotometer using distilled water as a reference. The solution was found to have a light transmittance at 430 nm of 96.0%.

The above-prepared granulated potassium sorbate was placed in a polyethylene bag, and the bag was sealed and was stored at room temperature of 20° C. for 2 years. After the storage, the granulated potassium sorbate was found to have a moisture content of 0.6% by weight and a light transmittance at 430 nm of 82.0%.

Other embodiments and variations will be obvious to those skilled in the art, and this invention is not to be limited to the specific matters stated above.

What is claimed is:

1. A granulated product of potassium sorbate with increased stability of hue having a reduction rate of light transmittance at a wavelength of 430 nm of equal to or less than 4.3% after storage at room temperature of 20° C. for two years, said granulated product (i) having a Na content of equal to or less than 450 ppm, or (ii) having an overall pore volume of equal to or less than 0.4 ml/g or a granule hardness of equal to or less than 15%, and a Na content of equal to or less than 1000 ppm.

2. A process for producing a granulated product of potassium sorbate with increased stability of hue having a reduction rate of light transmittance at a wavelength of 430 nm of equal to or less than 4.3% after storage at room temperature of 20° C. for two years by controlling a Na content to be equal to or less than 450 ppm, through the steps of:

neutralizing sorbic acid with a potassium hydroxide having a molar ratio of Na to K (Na/K) of equal to or less than 0.0024 to yield potassium sorbate; and granulating said potassium sorbate.

3. A process for producing a granulated product of potassium sorbate with increased stability of hue having a reduction rate of light transmittance at a wavelength of 430 nm of equal to or less than 4.3% after storage at room temperature of 20° C. for two years, said process comprising the steps of:

neutralizing sorbic acid with a potassium hydroxide to yield potassium sorbate, said potassium hydroxide having a molar ratio of Na to K (Na/K) of equal to or less than 0.006;

moisture-conditioning 100 parts by weight of said potassium sorbate with 1 to 8.5 parts by weight of water and 1 to 8 parts by weight of a water-soluble organic solvent; and subjecting the moisture-conditioned potassium sorbate to extrusion granulation.

4. A process for producing a potassium sorbate with increased stability of hue having a reduction rate of light transmittance at a wavelength of 430 nm of equal to or less than 4.3% after storage at room temperature of 20° C. for two years by controlling a Na content to be equal to or less than 1000 ppm, through the step of neutralizing sorbic acid with a potassium hydroxide having a molar ratio of Na to K (Na/K) of equal to or less than 0.006.

5. A granulated product of potassium sorbate with increased stability of hue, said granulated product having an overall pore volume of equal to or less than 0.4 ml/g, a Na content of equal to or less than 1000 ppm and a reduction rate of light transmittance at a wavelength of 430 nm of equal to or less than 4.3% after storage at room temperature of 20° C. for two years.

6. A method for the stabilization of a granulated product of potassium sorbate, with said method providing a higher stability of hue over time to the granulated product of potassium sorbate, and said method comprising the step of:

providing a granulated potassium sorbate having (i) an overall pore volume that is controlled to be equal to or less than 0.3 ml/g, (ii) an Na content that is controlled to be equal to or less than 450 ppm, or (iii) an overall pore volume that is controlled to be equal to or less than 0.4 ml/g or a granule hardness that is controlled to be equal to or less than 15%, and an Na content that is controlled to be equal to or less than 1000 ppm.

7. A process for producing a granulated product of potassium sorbate with increased stability of hue, said process comprising the step of subjecting an aqueous solution of potassium sorbate to fluidized bed granulation drying to yield a granulated product of potassium sorbate, said granulated product having (i) an overall pore volume of equal to or less than 0.3 ml/g, (ii) a Na content of equal to or less than 450 ppm, or (iii) an overall pore volume of equal to or less than 0.4 ml/g or a granule hardness of equal to or less than 15%, and a Na content of equal to or less than 1000 ppm.

* * * * *